United States Patent [19]

Mullins et al.

[11] Patent Number: 4,590,300
[45] Date of Patent: May 20, 1986

[54] PREPARATION OF ALLYLIC COMPOUNDS

[75] Inventors: Michael J. Mullins, Midland; Percy J. Hamlin, Beaverton, both of Mich.

[73] Assignee: The Dow Chemical Company, Midland, Mich.

[21] Appl. No.: 689,891

[22] Filed: Jan. 9, 1985

Related U.S. Application Data

[63] Continuation-in-part of Ser. No. 499,640, May 31, 1983, abandoned.

[51] Int. Cl.$^4$ ............................................. C07C 41/14
[52] U.S. Cl. .................................. 568/616; 568/673; 568/675; 568/689; 568/907; 568/908
[58] Field of Search ............... 568/616, 673, 675, 907, 568/908, 689

[56] References Cited

U.S. PATENT DOCUMENTS

| | | | |
|---|---|---|---|
| 2,434,394 | 1/1948 | Cheney et al. | 568/908 |
| 2,847,478 | 8/1958 | Hwa | 568/646 |
| 3,173,958 | 3/1965 | Milgrom et al. | 568/689 |
| 3,250,814 | 5/1966 | Stephenson | 568/675 |
| 4,368,337 | 1/1983 | Tawara et al. | 568/907 |

FOREIGN PATENT DOCUMENTS 913919 12/1962 United Kingdom ............... 568/675

OTHER PUBLICATIONS

Commereuc et al., *Bull Soc. Chim. France*, 652–656 (1974) (French) English translation provided with application.

*Primary Examiner*—Howard T. Mars
*Attorney, Agent, or Firm*—Douglas N. Deline; Norman L. Sims; Christopher J. Rudy

[57] ABSTRACT

Allyl methyl ethers are transetherified with alcohols by use of a catalyst of a solid acid that contains no mercury or cuprous salt catalyst.

20 Claims, No Drawings

PREPARATION OF ALLYLIC COMPOUNDS

CROSS-REFERENCE TO RELATED APPLICATION

This is a continuation-in-part of copending application Ser. No. 499,640, filed May 31, 1983 now abandoned.

BACKGROUND OF THE INVENTION

The present invention relates to the preparation of allylic compounds. More particularly, the present invention is a process for preparing allylic compounds by a transetherification reaction.

Transetherification reactions are extremely rare. Outside of certain specialized reactions, the process is not satisfactorily adapted to general use because of the difficulty in forming stable carbonium ion leaving groups from the ether starting reactants.

U.S. Pat. No. 2,847,478 (incorporated herein by reference) describes the unpressurized transetherification of diallyl ether with alcohols employing a homogeneous catalyst system comprising a salt of mercury and a strong acid cocatalyst. It is taught that the presence of the homogeneous acid alone is not sufficient to catalyze the reaction. The process is not well suited to commercial implementation due to the toxic nature of the mercury-containing catalysts.

British Pat. No. 913,919 and U.S. Pat. No. 3,250,814 (both incorporated herein by reference) describe the unpressurized preparation of allyl ethers by reacting allyl alcohols or organooxyallyl alcohols and by reacting diallyl ether with aliphatic alcohols, respectively. Both references teach the use of a catalyst system of a cuprous salt and an acid cocatalyst. Neither reference teaches that an acid alone, whether homogeneous or heterogeneous, is sufficient to catalyze the reactions. Cuprous salts, too, are by nature toxic.

SUMMARY OF THE INVENTION

According to the present invention, there is provided a convenient process for preparing an allylic compound corresponding to the formula:

XHC=CHY wherein X is $RCH_2$— or $RCH_2CH(OR')$— and Y is —$CH_2OR'$ or hydrogen, and when X is $RCH_2$—, Y is —$CH_2OR'$ and when X is $RCH_2CH(OR')$—, Y is hydrogen, where R is hydrogen or an alkyl moiety having from 1 to about 20 carbons and R' is a $C_{1-20}$ moiety corresponding to the formula (CHRCHRO$)_n$R wherein R is as previously defined and n is an integer from zero to about 10, comprising contacting an allyl methyl ether corresponding to the formula:

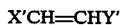
X'CH=CHY' wherein X' is $RCH_2$— or $RCH_2CH(OCH_3)$— and Y' is —$CH_2OCH_3$ or hydrogen, and when X' is $RCH_2$—, Y' is —$CH_2OCH_3$ and when X' is $RCH_2CH(OCH_3)$—, Y' is hydrogen where R is as previously defined, with a primary or secondary alcohol, or a (poly)alkylene glycol or monoalkyl ether thereof corresponding to the formula HO(CHRCHRO$)_n$R where R is as previously defined, in the presence of a catalytic amount of a heterogeneous strong acid that contains no mercury or cuprous salt catalysts at an elevated temperature such that the allylic compound is produced.

The products of the invented process are valuable solvents and monomers that may be polymerized by means of the ethylenic unsaturation to prepare molded articles. Furthermore, the compounds of the invented process may be easily hydrogenated by contacting with hydrogen and a noble metal catalyst under hydrogenating conditions to yield valuable ether solvents.

DETAILED DESCRIPTION OF THE INVENTION

The allyl methyl ethers for use in the present process are suitably prepared by use of chelated phosphine nickel catalyzed reaction of conjugated dienes or mixtures thereof and methanol. A particular example of a suitable nickel catalyst is the reaction product of 1,2-bis(diphenylphosphino)ethane and bis(cyclooctadiene)-nickel. The reaction is conveniently conducted in a metal or glass lined reactor at elevated temperatures and pressures on the order of 50° C.–250° C. and 50–500 psig.

According to one embodiment of the process, the conjugated diene is butadiene, pentadiene or a mixture thereof. The diene may be part of a mixture of hydrocarbons optionally including alkanes and alkenes, for example, a mixture of petroleum light gases or crude olefin streams produced from crude oil cracking plants. In this embodiment of the invention, the conjugated diene is conveniently reacted and separated away from the remaining olefins and the product is employed in the present invented process to prepare valuable solvents all without the generation of salt streams or other by-products. Preparation of allyl methyl ethers for use in the present process according to the above-described process has been previously disclosed and claimed in copending application Ser. No. 517,548, filed July 27, 1983, a continuation-in-part of application Ser. No. 368,537, filed Apr. 13, 1983, now abandoned.

Another method of preparing the allyl methyl ethers for use in the present process which is known in the art is disclosed by Commereuc et al., *Bull Soc. Chim. France*, 652-56 (1974) (French; English translation provided with application), and is incorporated herein by reference.

Preferred allyl methyl ethers are those derived from butadiene and pentadiene, e.g., 3-methoxy-1-butene, 1-methoxy-2-butene, 3-methoxy-1-pentene and 2-methoxy-3-pentene, or a mixture thereof. Under the conditions of the present invention, the reaction product is an equilibrium mixture of the branched and linear isomers. Generally, about equal molar amounts of each isomer are present in the resulting product mixture regardless of the ratio of reactant isomers. Apparently under the influence of the present reaction conditions allyl and ether functional groups rearrange until equilibrium concentrations of each are reached. The isomers may easily be separated if desired by standard techniques such as distillation.

The primary or secondary alcohols, (poly)alkylene glycols or ethers thereof for use according to the present process are of course well-known and readily available. Preferred compounds are primary alcohols, ethylene glycol, propylene glycol, diethylene glycol, dipropylene glycol and lower alkyl ethers thereof.

The catalysts for use in the present invention are solid acids that contain no mercury or cuprous salt catalysts. Included are strong acid-exchanged polymeric ion-exchange resins, particularly macroporous ion-exchange resins such as a sulfonated macroporous styrene-divinylbenzene copolymers. Additionally included are other types of polymeric ion-exchange resins such as perfluoroethylene polymers, acidic clays, acid treated silica or alumina and acid form zeolites, including both naturally occurring and artificial zeolites. A preferred catalyst is a sulfonated macroporous polystyrene divinylbenzene copolymer. The catalyst is present in an amount by weight based on allyl methyl ether of from about 0.1 percent to about 10 percent. A catalytic amount of a heterogeneous strong acid that contains no mercury or cuprous salt catalysts means that any impurities of mercury or cuprous salts that might be present are present at levels that are not catalytic for the preparation of the allylic compounds described herein.

The reaction is conducted at elevated temperatures above ambient temperature such that the allylic compounds are produced, preferably from about 50° C. to about 200° C., and more preferably from about 60° C. to about 150° C. Reaction times are generally from about ½ hour to about 4 hours depending on the nature of the reactants and the reaction temperature.

Pressures of reaction employed are those that result in the formation of the allyl compound. The reaction may suitably be conducted in a sealed reaction vessel whereby the reaction pressure may vary from about atmospheric to about 1000 psig. Pressures from about 50 psig to about 300 psig and from about 100 psig to about 200 psig are commonly employed and are the more and most preferred ranges. As an option, an inert reaction atmosphere may be employed particularly where light colored products are desired. A preferred inert reaction atmosphere is argon gas. As a further option, a solvent, especially one able to form azeotropes with the compounds formed by the invention, may also be present. Preferred solvents include hydrogenated derivatives of the present allylic compounds.

According to one embodiment of the invention the by-product methanol is removed from the reaction mixture during the course of the reaction, thereby driving the reaction toward the desired product. Where conversion is not limited to equilibrium conditions, very high yields approaching 90–95 percent are attained.

The product may be recovered by standard distillative techniques or any other suitable means of separation.

SPECIFIC EMBODIMENTS

Having described the invention, the following examples are provided as further illustrative thereof and are not to be construed as limiting inasmuch as obvious modifications thereof will be readily apparent to the skilled artisan.

EXAMPLE 1

A 500-ml autoclave of 316 stainless steel is charged with the following reactants under an argon atmosphere: methanol (100 ml, 2.47 moles), 1,2-bis(diphenylphosphino)ethane (800 mg, 2.0 mmoles), bis(1,5-cyclooctadiene)nickel (300 mg, 1.1 mmoles), t-butylbenzene (1.0 g internal standard for quantitative gas chromatograph analysis) and butadiene (5 g). The autoclave is then heated to about 120° C. and the pressure maintained at about 140–170 psig by periodic addition of butadiene. After 5 hours, the reaction is stopped. Analysis by gas chromatograph indicates a quantitative yield of 3-methoxy-1-butene and 1-methoxy-2-butene (ratio 1.6:1). Total addition of butadiene is about 26 g.

After distillation, about 10 g of the resulting mixture of isomers and methanol (86 percent by weight methoxybutenes, 13.5 percent methanol) is combined in an autoclave with propylene glycol (10.0 g, 131 mmoles), macroporous sulfonated styrene-divinylbenzene copolymeric beads (Dowex ® MSC-1-H) (1.0 g) and t-butylbenzene (173.4 mg) (used again as an internal standard). The reactor is sealed and heated to about 100° C. After about 1.6 hours, the reactor is cooled and opened.

Analysis indicates the product mixture comprises four isomeric reaction products, e.g., 3-(2-hydroxy-1-propoxy)-1-butene, 3-(1-methyl-2-hydroxyethoxy)-1-butene, 1-(2-hydroxy-1-propoxy)-2-butene and 1-(1-methyl-2-hydroxyethoxy)-2-butene. Selectivity based on propylene glycol is 76 percent at an equilibrium limited conversion of 41 percent.

EXAMPLE 2

The reaction conditions of Example 1 are substantially repeated excepting that 2-methoxyethanol (7.08 g, 93 mmoles) is employed as the alcohol for transetherification with a mixture comprising 3-methoxy-1-butene, 1-methoxy-2-butene (ratio 4.64:1), methanol and octatriene oligomers. The weight ratio of components in the mixture is 75.4 percent ethers, 23.4 percent methanol and 1.2 percent octatriene isomers, and is representative of the reaction product of a butadiene gas stream with methanol in the presence of a chelated phosphine nickel (0) catalyst.

The reactants are combined in an autoclave under air atmosphere along with t-butylbenzene internal standard, and about 2 percent by weight of all reactants of sulfonated styrene-divinylbenzene beads (Dowex ® MSC-1-H). The reactants are heated to about 100° C. for 3.5 hours. Analysis indicates about 22 percent of 2-methoxyethanol is consumed. The product (2.71 g, 100 percent selectivity) comprised 53 percent by weight 3-(2-methoxyethoxy)-1-butene and 47 percent by weight 1-(2-methoxyethoxy)-2-butene.

EXAMPLE 3

The reaction conditions of Example 1 are substantially repeated excepting that the alcohol reactant is diethylene glycol monobutyl ether and the allyl ether is a mixture of 3-methoxy-1-butene, 1-methoxy-2-butene and methanol (ratio of ethers to methanol equals 95:5). The catalyst is Dowex ® MSC-1-H, 2.5 percent by weight. After heating at about 100° C. for 2 hours, analysis by capillary gas chromatograph indicates a 100 percent selectivity to the desired transetherification product at a conversion of about 28 percent. Analysis indicates the products correspond to the formulas:

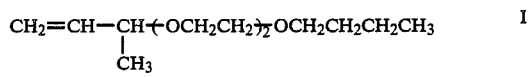

and

EXAMPLE 4

Hydrogenation

A sample of the reaction mixture of Example 1 (5.0 g, 88 percent ethers by weight), 12 percent propylene glycol) is combined with 20 ml of methanol, 100 mg of 5 percent Pd on carbon catalyst in a pressure reactor and treated with hydrogen (60 psig, 25° C.) for 14 hours. After hydrogenation the resulting suspension is filtered using diatomaceous earth. The methanol is removed by evaporation and the product distilled. The resulting product mixture (4.18 g, 88 percent yield) has a boiling point of 65°–80° C. at 24 torr. Purity is 94 percent. The product contains 4 isomers: 3-(2-hydroxy-1-propoxy)butane, 3-(1-methyl-2-hydroxyethoxy)butane, 1-(2-hydroxy-1-propoxy)butane and 1-(1-methyl-2-hydroxyethoxy)butane.

What is claimed is:

1. A process for preparing an allylic compound corresponding to the formula $$XHC=CHY$$

wherein X is $RCH_2-$ or $RCH_2CH(OR')-$ and Y is $-CH_2OR'$ or hydrogen, and when X is $RCH_2-$, Y is $-CH_2OR'$ and when X is $RCH_2CH(OR')-$, Y is hydrogen, where R is hydrogen or an alkyl moiety having from 1 to about 20 carbons and R' is a $C_{1-20}$ moiety corresponding to the formula $(CHRCHRO)_nR$ wherein R is as previously defined and n is an integer from zero to about 10, comprising contacting an allyl methyl ether corresponding to the formula $$X'HC=CHY'$$

wherein X' is $RCH_2-$ or $RCH_2CH(OCH_3)-$ and Y' is $CH_2OCH_3$ or hydrogen and when X' is $RCH_2-$, Y' is $-CH_2OCH_3$ and when X' is $RCH_2CH(OCH_3)-$, Y' is hydrogen where R is as previously defined, with a primary or secondary alcohol, or a (poly)alkylene glycol or monoalkyl ether thereof corresponding to the formula $HO(CHRCHRO)_nR$ in the presence of a catalytic amount of a catalyst present in an amount by weight based on allyl methyl ether of from about 0.1 percent to about 10 percent, consisting essentially of a solid heterogeneous strong acid that contains no mercury or cuprous salt catalysts at an elevated temperature such that the allylic compound is produced.

2. A process according to claim 1 wherein the pressure is from about atmospheric to about 1000 psig.

3. A process according to claim 2 wherein the temperature is from about 50° C. to about 200° C.

4. A process according to claim 3 wherein the pressure is from about 50 psig to about 300 psig.

5. A process according to claim 4 wherein the temperature is from about 60° C. to about 150° C.

6. A process according to claim 5 wherein the pressure is from about 100 psig to about 200 psig.

7. A process according to claim 1 conducted in an inert reaction atmosphere.

8. A process according to claim 1 wherein the (poly)alkylene glycol or monoalkyl ether thereof is selected from the group consisting of ethylene glycol, propylene glycol, diethylene glycol, dipropylene glycol and lower alkyl ethers thereof.

9. A process according to claim 1 wherein the allyl methyl ether is selected from the group consisting of 3-methoxy-1-butene, 1-methoxy-2-butene, 3-methoxy-1-pentene, 2-methoxy-3-pentene and mixtures thereof.

10. The process according to claim 1 wherein the catalyst is selected from the group consisting of strong acid-exchanged polymeric ion-exchange resins, acidic clays, acid treated silica, acid treated alumina, and acid form zeolites.

11. A process according to claims 1, 2, 3, 4, 5, 6, 7, 8 or 9 wherein the catalyst is a sulfonated macroporous styrene-divinylbenzene copolymer in the acid form.

12. A process according to claim 1, 3, 5, 2, 4, 6, 7, 8, 9 or 10 wherein the temperature is about 100° C. or above.

13. A process according to claim 12 wherein the catalyst is a sulfonated macroporous styrene-divinylbenzene copolymer in the acid form.

14. A process according to claim 6 wherein
(a) the (poly)alkylene glycol or monoalkyl ether thereof is selected from the group consisting of ethylene glycol, propylene glycol, diethylene glycol, dipropylene glycol and lower alkyl ethers thereof;
(b) the allyl methyl ether is selected from the group consisting of 3-methoxy-1-butene, 1-methoxy-2-butene, 3-methoxy-1-pentene, 2-methoxy-3-pentene and mixtures thereof; and
(c) the catalyst is a sulfonated macroporous styrene-divinylbenzene copolymer in the acid form.

15. A process according to claim 14 wherein methanol is removed as a by-product during the course of the reaction.

16. A process according to claim 15 wherein the yield is about 90 percent or above.

17. A process according to claim 14 wherein the temperature is about 100° C.

18. A process according to claim 15, 16 or 17 conducted in an inert reaction atmosphere.

19. A process according to claim 18 wherein the inert reaction atmosphere is argon.

20. A process according to claim 7 wherein the inert reaction atmosphere is argon.

* * * * *